United States Patent [19]

Pagani

[11] Patent Number: 4,613,697

[45] Date of Patent: Sep. 23, 1986

[54] PROCESS FOR THE DISPLACEMENT TO THE GASEOUS PHASE OF THE EXCESS OF NH₃ CONTAINED IN AN AQUEOUS UREA SOLUTION

[75] Inventor: Giorgio Pagani, Milan, Italy

[73] Assignee: Montedison S.p.A., Milan, Italy

[21] Appl. No.: 686,383

[22] Filed: Dec. 26, 1984

Related U.S. Application Data

[63] Continuation-in-part of Ser. No. 500,992, Jun. 3, 1983, abandoned, and a continuation-in-part of Ser. No. 629,486, Jul. 10, 1984, abandoned.

[30] Foreign Application Priority Data

Jun. 8, 1982 [IT] Italy ................. 21774 A/82
Jul. 14, 1983 [IT] Italy ................. 22073 A/83

[51] Int. Cl.⁴ ............... C07C 126/02; C07C 126/08
[52] U.S. Cl. ........................... 564/67; 564/66; 564/70; 564/71; 564/73
[58] Field of Search ............... 564/67, 70, 71, 73, 564/66

[56] References Cited

U.S. PATENT DOCUMENTS 3,232,984 11/1961 Finneran ................. 564/70

FOREIGN PATENT DOCUMENTS 1113961 12/1981 Canada .
18285 11/1964 Japan ................. 564/71

OTHER PUBLICATIONS

Hydrocarbon Processing–Nov. 1982, pp. 87-91, Pagani.
Patents Act 1952-1955–Sep. 1, 1960, Chemical Construction Corporation.

Primary Examiner—Charles F. Warren
Assistant Examiner—R. A. Picard
Attorney, Agent, or Firm—Stevens, Davis, Miller & Mosher

[57] ABSTRACT

A process for the displacement to the gaseous phase, at 80-250 Kg/cm², of the excess $NH_3$ contained in an aqueous urea solution, coming, at 150°-230° C., from a former stripping, isobaric with the urea synthesis, and containing also $CO_2$ as ammonium carbamate. The $CO_2$ is, at most, 25% b.w. of the urea, and the displacement is performed by means of a $CO_2$ stripping within a falling-film exchanger, hereinafter called the $CO_2$ stripper, isobaric too with said synthesis. The amount of carbamate leaving the bottom of said $CO_2$ stripper is substantially equal to the amount of carbamate entering the same stripper. The global $NH_3:CO_2$ ratio, in the solution entering the $CO_2$ stripper, is from 2 to 8 b.w. and heat is supplied only to the uppermost portion of the pipes of the $CO_2$ stripper, wherein the surface ratio between the lowermost portion and said uppermost portion is at least 1:1 and wherein the residence time ratio between said lowermost portion and said uppermost portion is at least 1/1, the residence time in said uppermost portion being from 1 to 3 s.

15 Claims, 6 Drawing Figures

PROCESS FOR THE DISPLACEMENT TO THE GASEOUS PHASE OF THE EXCESS OF $NH_3$ CONTAINED IN AN AQUEOUS UREA SOLUTION

This application is a Continuation-In-Part of my prior applications Ser. No. 500,992, filed June 3, 1983, and Ser. No. 629,486 filed July 10, 1984, and both now abandoned.

BACKGROUND OF THE INVENTION

The improvements in urea manufacturing plants have allowed, until now, the lowering of the steam consumption from 1500 to 1000 Kg per ton of urea or, in the best case, 550–600 Kg/t; U.S. Pat. No. 4,208,347 deals with a new, double loop, process (I.D.R process), but describes only the high pressure loop without detailing much about the final, low pressure, unit (the so called "finishing").

The Applicant [See: "New process gives urea with less energy" (Hydrocarbon Processing, Nov. 1982)] described later an I.D.R. complete manufacturing line, "finishing" included, comprising a high pressure loop (reactor, two subsequent isobaric strippers and a carbamate condenser) and a "finishing" comprising:

I-a medium pressure still (20–30 ata), the vapors of which are condensed within a vacuum concentrator, substantially at 0.35 ata (see item II), thus realizing a multiple-effect evaporation, and a low pressure still, working substantially at 5 ata (atmospheres, absolute).

II-a two-step vacuum concentration section (respectively—and approximately—at 0.35 and 0.05 ata) and one unit for the recovery of $NH_3$ from the reaction waters and from the scrubber waters coming from the washing of the synthesis vent.

The steam consumption of the complete I.D.R. line was slightly lower than 500 Kg/t and a further decrease to 500 Kg/t was forecast.

The present invention relates to an improved process for the manufacture of urea, which process permits much lower steam consumption of said I.D.R. line in a new and original way; in other words the high pressure loop and the finishing unit were first modified and then matched in an original way, so as to improve synergistically the whole I.D.R. line, while lowering the (outside) steam requirement to heretofor unimaginable levels.

DISCLOSURE

In its most general form, the invention concerns an improved high pressure loop of the I.D.R. process and more precisely a process for the displacement to the gaseous phase, at 80–250 Kg/cm², of the excess $NH_3$ contained in an aqueous urea solution, coming, at 150°–230° C., from a former stripping, isobaric with the urea synthesis, and containing also $CO_2$ as ammonium carbamate, the $CO_2$ being at most 25% b.w. of the urea, wherein the displacement is performed by means of a $CO_2$ stripping within a falling-film exchanger, hereinafter $CO_2$ stripper, isobaric too with said synthesis, the amount of carbamate leaving the bottom of said $CO_2$ stripper being substantially equal to (or comprised between 100 and 150% of) the amount of carbamate entering the same stripper, characterized in that the global $NH_3$:$CO_2$ ratio, in the solution entering the $CO_2$ stripper, is from 2 to 8 b.w. and in that heat is supplied only to the uppermost portion of the pipes of the $CO_2$ stripper, wherein the surface ratio between the lowermost portion and said uppermost portion is at least 1:1 and wherein the residence time ratio between said lowermost portion and said uppermost portion is at least 1/1, the residence time in said uppermost portion being from 1 to 3 s.

Said solution, containing less than 25% b.w. of carbamate, comes from at least one preceeding isobaric stripping, for instance an $NH_3$ isobaric stripping; the invention however can be used not only in those double stripping loops in which the strippings are isobaric with the synthesis, but also in those loops in which one or both the strippings are at either a lower or different pressure, always with respect to the synthesis. In any case the instant invention is always valuable when the main purpose is to transfer into the gaseous phase the free $NH_3$ contained in an aqueous urea solution, at a rather high pressure, while using, as stripping agent, part or all of the carbon dioxide required by the urea synthesis.

The teaching of Canadian Pat. No. 1,113,961 is to heat strongly the uppermost portion of the tubes of a $CO_2$ stripper and to keep the residence time of the process fluid, in said heated uppermost portion, at a much higher level (5 seconds) with respect to the residence time (from 1 to 2 s) in the underlying portion, cooled or adiabatic, just in order to "decompose" as much residual carbamate as possible.

To the contrary, in the present invention the residence time in the uppermost and heated portion must be lower (from 1 to 3 s) with respect to the underlying adiabatic portion (from 3 to 5 s) and the temperature drops, in said underlying portion (partially because of the $CO_2$ addition), down to a level between 150° and 210°, preferably 160° and 190° and even better 160° and 175° C., the temperature of the $CO_2$, injected as a stripping agent, being preferably from 80° to 140° C.

All this can be carried out, by heating only a small portion of the length of the tubes, namely a portion equal to or lower than ½ (preferably ⅓) and even better from 1/5 to ⅓ of the whole length, the underlying portion, substantially adiabatic, being obviously the complement to 1. The invention allows one to reach excellent and unexpected results as to thermal balance, steam requirement and absence of corrosion; it further allows one to stop completely and safely the degrading hydration of urea to carbamate, according to the equation:

$$NH_2-CO-NH_2 + H_2O \rightarrow NH_2-COONH_4.$$

Best results are reached when the ratio between the exchanging surface of the $CO_2$ stripper ($S_{CO2}$) and the exchanging surface ($S_{NH3}$) of the preceding stripper is given by the expression: $A = S_{CO2}/S_{NH3} < 1$.

A particular and advantageous form of the invention is a process for the displacement, from the liquid to the gaseous phase, at pressures from 130 to 220 Kg/cm², of the excess $NH_3$ contained in an aqueous urea solution having a temperature from 190° to 220° C., characterized in that:

(a) the $NH_3$:$CO_2$ ratio, in the solution fed to the $CO_2$ stripper, is from 3 to 6 (preferably 4 to 5.5) b.w.;

(b) heat is supplied only to the uppermost portion of the tubes of the $CO_2$ stripper, wherein the ratio between the surface of the lowermost portion and the surface of the uppermost portion of the tubes is at least 2:1 (preferably from 2:1 to 4:1) and wherein the ratio between the residence time of the solution to be stripped in said lowermost portion and the residence time in said uppermost portion is at least 2:1 (preferably from 2:1 to 4:1), said residence time in the lowermost portion of the tubes being at least 3.5 (preferably from 3.5 to 5) s and said residence time in the uppermost portion being from 1.5 to 2.5 s.

BRIEF DESCRIPTION OF THE DRAWINGS

The process is still further illustrated by the accompanying FIG. 1, representing a simplified flow-sheet of the process itself; the detailed description of such figure is reported in example 1.

FIGS. 2-6 are described in examples 3-6.

PREFERRED EMBODIMENTS

According to a preferred embodiment (see FIG. 2), the invention concerns an I.D.R. process for the manufacture of urea, comprising two subsequent loops, wherein:
(A) in the first (high pressure) loop the solution coming from the synthesis zone contains, after the first isobaric stripper of said I.D.R. process (E1), a strong $NH_3$ excess ($NH_3:CO_2 \geq 6$ by moles) and a low $CO_2$ percentage ($CO_2:urea \leq 25\%$ b.w.) and contains, before the second isobaric stripper (E2) of said I.D.R. process, an amount of ammonium carbamate (CBE) comprised from 100 to 150% of the amount of carbamate (CBU) contained in the solution leaving the same (E2) stripper, wherein the consequent overproduction of carbamate (in E2) releases such an amount of heat to displace a major proportion of the residual $NH_3$ excess contained therein, that allows a drastic reduction of the steam wasted in (E2);
(B) in the second (low pressure) loop, the solution leaving (E2) is flashed at 20-30 ata and enters a first (medium pressure) still (E3), heated indirectly and completely by a low pressure recovery steam, coming from the isobaric condensation (in E8) of the vapors leaving the top of (E2), said recovery steam having such a thermal level to decompose at least said overproduction of carbamate, originated in (E2);
(C) the solution leaving (E3) is flashed substantially at 5 ata and enters a second (low pressure) still (E4) and then a vacuum concentrator (E5), wherein the heat of the vapors leaving the head of (E3), rich in $NH_3$ and $CO_2$, is exploited for the working run of (E4) and (E5).

Said second isobaric stripper (E2) is a falling-film tube-bundle heat exchanger, where the solution to be stripped meets a countercurrent stream of $CO_2$, injected from outside, the pipes being heated by condensing steam only in their uppermost portion; wherein such stripper was previously described in the first pages of the instant specification.

Said embodiment is particularly advantageous when:
The pressure of the "high pressure" loop is from 120 to 250 Kg/cm².
The temperature of the solution leaving the first isobaric stripper (E1) is substantially from 150° to 230° C.
Said $NH_3:CO_2$ molar ratio of the solution leaving the first isobaric stripper E1 ($\geq 6$ by moles) concerns the total amounts of $NH_3$ and $CO_2$, also if chemically bound (e.g. as carbamate), but for the amounts bound in the form of urea.
Said recovery steam (coming from E8) is at a pressure $\geq 6.5$ absolute atmospheres.

The usual working pressure of the process side of said vacuum concentrator (E5) is approximately 0.35 absolute atmospheres.

DETAILED DESCRIPTION OF THE INVENTION

Because of the high yields of the I.D.R. process, the ratio between the fresh $CO_2$, fed to the second isobaric stripper ($CO_2$ inj.), and the carbamate (CBE) entering the same stripper attains a very high level; in general: ($CO_2$ inj.):(CBE)>2 (by moles).

The solution leaving (E5) must be furtherly concentrated in (E6) (as an optional and advantageous way of performing the invention) exploiting the heat of the recovery steam hereinabove and the resulting concentrated solution (urea=90-95% b.w.) is transferred to the final vacuum concentrator (E7); the vapors leaving the vacuum concentrators (E5, E6 and E7), containing some amount of $NH_3$ and $CO_2$, are then condensed in an usual way and a recovery tower (C3) allows one to obtain a recovery stream to be condensed (in E11), together with the vapors coming from said still (E4). The resulting condensate is recycled to said (E4) still (shell side); the condensed vapors leaving (E5) are recompressed (by pump PC1) and recycled to the high pressure loop.

The first isobaric stripper (E1) of the I.D.R. process can be advantageously a vertical heat exchanger having a tube bundle and being selected from the group comprising the so called "falling-film" and "upflow" exchangers. The supply of steam (at 18-30 ata) to said second isobaric stripper (E2) may be also lowered down to zero, performing thereby a purely adiabatic stripping. The determination of the size of said second (E2) stripper is one of the most ticklish problems of the whole process; wherein the ratio R:

$$R = \frac{\text{uppermost surface of the pipes, heated by condensing steam}}{\text{remnant portion of the surface of the pipes}}$$

should be $R \leq 1$ and preferably from $\frac{1}{2}$ to $\frac{1}{4}$; in other words, the uppermost surface of the tubes should be from $\frac{1}{2}$ to 1/5 (preferably from 1/5 to $\frac{1}{3}$) of the total surface.

The residence time of the urea solution, infact, in said uppermost portion of the exchanger must be very short, namely from 1 to 3 s (preferably from 1.5 to 2.5 s), the ratio:

$$\frac{\text{residence time in the lowermost portion}}{\text{residence time in the uppermost portion}}$$

being thus $\geq 1$ (pref. $\geq 2$, even better $\geq 4$); furtherly the ratio between the exchanging surface ($S_{CO_2}$) of said stripper (E2) and the exchanging surface ($S_{NH_3}$) of said stripper (E1) must be preferably greater than one, namely:

$$S_{CO_2}:S_{NH_3} \geq 1:1.$$

According to a further embodiment of the invention, it is advantageous to carry out a process in which:
(a) the urea synthesis is performed at 150°-250° C. and 170-220 atmospheres;
(b) the temperature of the solution entering said second stripper (E2) is from 190° to 220° C.;
(c) the temperature of the solution leaving the bottom of the same stripper (E2) is from 150° to 190° C., preferably from 160° to 190° C. and even better from 160° to 175° C.;

(d) the temperature of the $CO_2$, injected as a stripping agent into the same stripper (E2), is from 80° to 140° C.;

(e) the solution leaving said first stripper (E1) and entering said second stripper (E2) contains such a low amount of $CO_2$ that:

$CO_2$: urea $\leq$ 22% b.w.;

(f) the $NH_3$:$CO_2$ molar ratio, in said solution entering said second stripper (E2), is equal to or higher than 10:1.

The condensation pressure in (E5), and consequently also in (E4), of the heating vapors coming from (E3) is very low; therefore the pressure of the solution to be distilled in (E3) can be lowered to such a small level that the heating of the same still (E3) can be carried out by means of recovery steam (at 6.5-9 ata) coming from condenser (E8).

The lowest temperature of the whole low-pressure loop (about 90° C.) is registered at the inlet of the first vacuum concentrator (E5), whereafter the temperature increases (gradually) with the degree of concentration of the final urea solution; that's why the condensation temperature on the shell side of said concentrator (E5) is very low too (115°-120° C.) and that's why, consequently, the pressure of the whole low-pressure loop can be kept at a lower level.

The present inventor found it very advantageous to transfer a portion of the thermal load from said second stripper (E2) to the first medium-pressure still (E3), this last apparatus, because of a lower working pressure and being heated, very advantageously, by recovery steam; all this is the counterbalance of fact that the very satisfactory stripping of $NH_3$ in said stripper (E2) is bound to the parallel formation of carbamate, the amount of which carbamate, at the outlet of stripper (E2), is greater than at the inlet.

Such expedient is quite satisfactory, not only when performed within an I.D.R. process, in a narrow sense, but also when performed in those double-stripping processes in which the second stripper (E2) (in countercurrent with $CO_2$) is working at a pressure slightly different (some tens of atmospheres) from the pressure of the first stripper (E1); see e.g. Italian patent publication No. 24357 A/80. In the foregoing embodiment the two strippers (E1) and (E2) are isobaric with each other and with the synthesis reactor, but for the pressure drops bound to hydraulics (and similar); as it is known, according to the equation:

$CO_2 + 2NH_3 \rightarrow NH_2-CO-NH_2 + H_2O$

300 Kg of water are by-produced per ton of urea and such water is removed, for the most part, within two groups of vacuum concentrators, working at a different degree of vacuum.

According to the prior art the vapors coming from said concentrators, containing 5-7% b.w. $NH_3$ and 2-3% b.w. $CO_2$, were condensed and pumped to a recovery tower (C3 in FIG. 2), as to recover the $NH_3$ therein contained to lower down the amount of residual $NH_3$—in the waste waters—at least to 100-200 ppm, while obtaining, from the head of the same tower C3, vapors containing 25-30% b.w. $NH_3$ (depending on the working pressure) and these vapors were condensed and recycled; the steam required by such a recovery unit was approximately 120 Kg/t of urea. Our new low-pressure loop (see FIG. 3) is an advantageous alternative, with respect to the prior art, illustrated in the dotted lines of FIG. 2 process, in that said steam consumption (120 Kg/t) can be completely suppressed.

According to the advantageous alternative (illustrated in FIG. 3), the vapors coming from the vacuum concentrator (E6) are condensed within a water-cooled apparatus (E13), whereinto is conveyed also a portion of the vapors (15) coming from the final vacuum concentrator (E7) (previously compressed in EJ2), the remnant portion (25) being fed, as a liquid phase, to the recovery tower (C3); the gist of such an alternative resides in that said (C3) tower contains a vertical falling-film tube-bundle, heated by the vapors (11) coming from said low-pressure still (E4), and in that the vapors (26), containing $NH_3$ and coming from said (C3) tower, are condensed too within said water-cooled apparatus (E13), whereafter the liquid condensate (27) leaving said apparatus (E13) is recycled to said tower (C3), the bottom of which tower, practically free from $NH_3$ and usually at 70°-72° C., is partially wasted (line 30) and partially (line 29) utilized for the scrubbing of the synthesis vent (22).

The vapors (rich in recovered $NH_3$) leaving said apparatus (E13) (see line 31 in FIG. 4) shall be treated in an usual way; they can be precondensed in E14, compressed, for instance, by a vacuum pump PV1 (e.g. at 1-1.5 Kg/cm², absolute) and then condensed (in E15), further compressed (by pump PC2), cooled in (E16) and recycled to said low-pressure still (E4), together with the scrubbing liquid (35) from tower (scrubber) (C2). The steam consumption is thus suppressed, while getting a slightly higher power need, (approximately 2 Kwh per t of urea).

Figure 4:
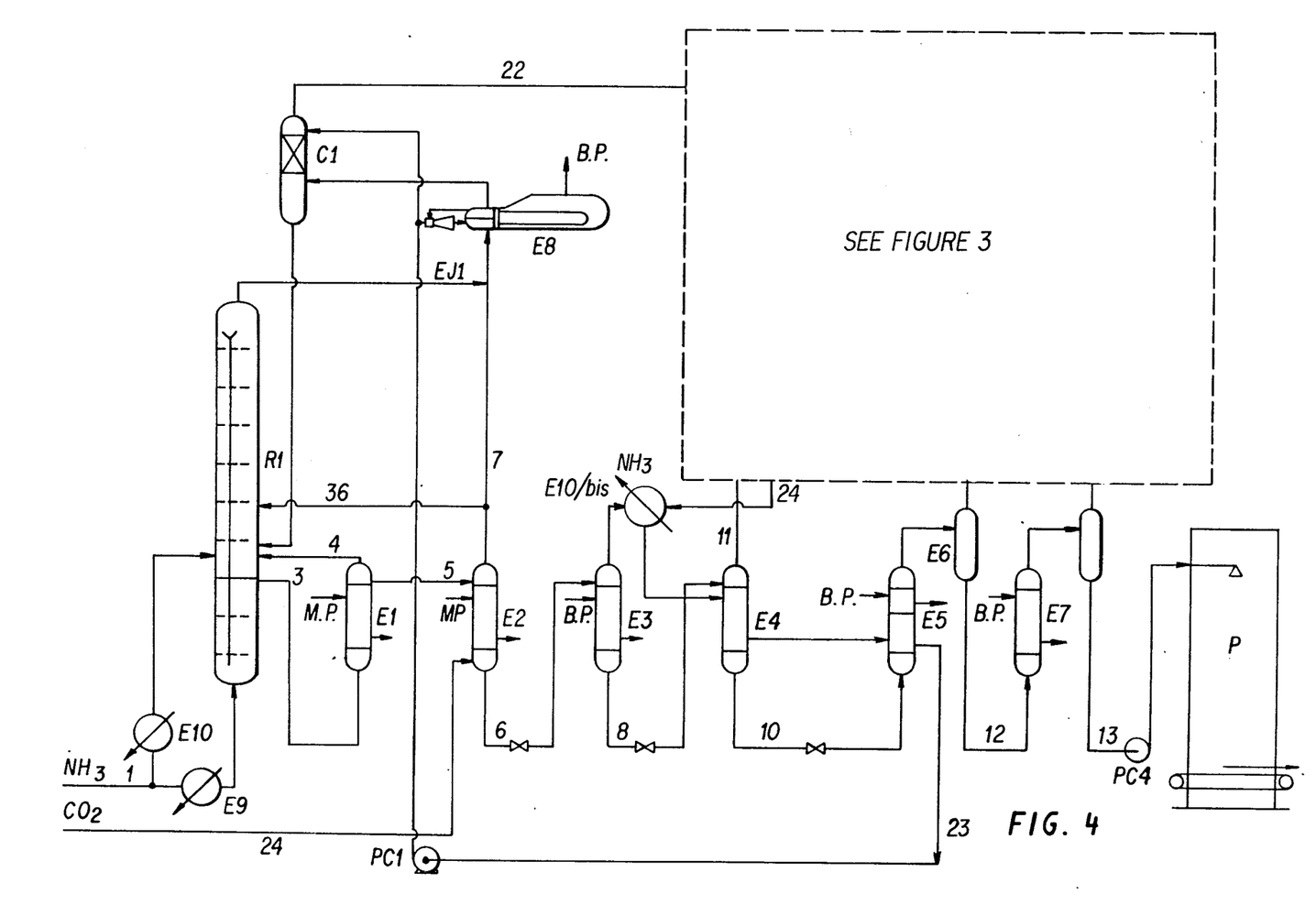

The performance of said apparatus (E13) can be surprisingly improved, when using, as shown in FIG. 4, a vertical exchanger, containing a tube bundle, wherein the cooling medium, e.g. $H_2O$, flows within the bundle pipes, said exchanger being characterized in that the vapors to be (at least partially) condensed enter the lowermost portion of the shell and leave the same shell in its uppermost portion, thus flowing in countercurrent to the liquid condensate, which falls downwards, at least partially along the outer surface of the pipes, and which leaves the lowermost portion of said shell, in a lower position, with respect to the inlet of the vapors.

The following examples illustrate further the invention, without limiting the scope thereof.

EXAMPLE 1

Figure 1:
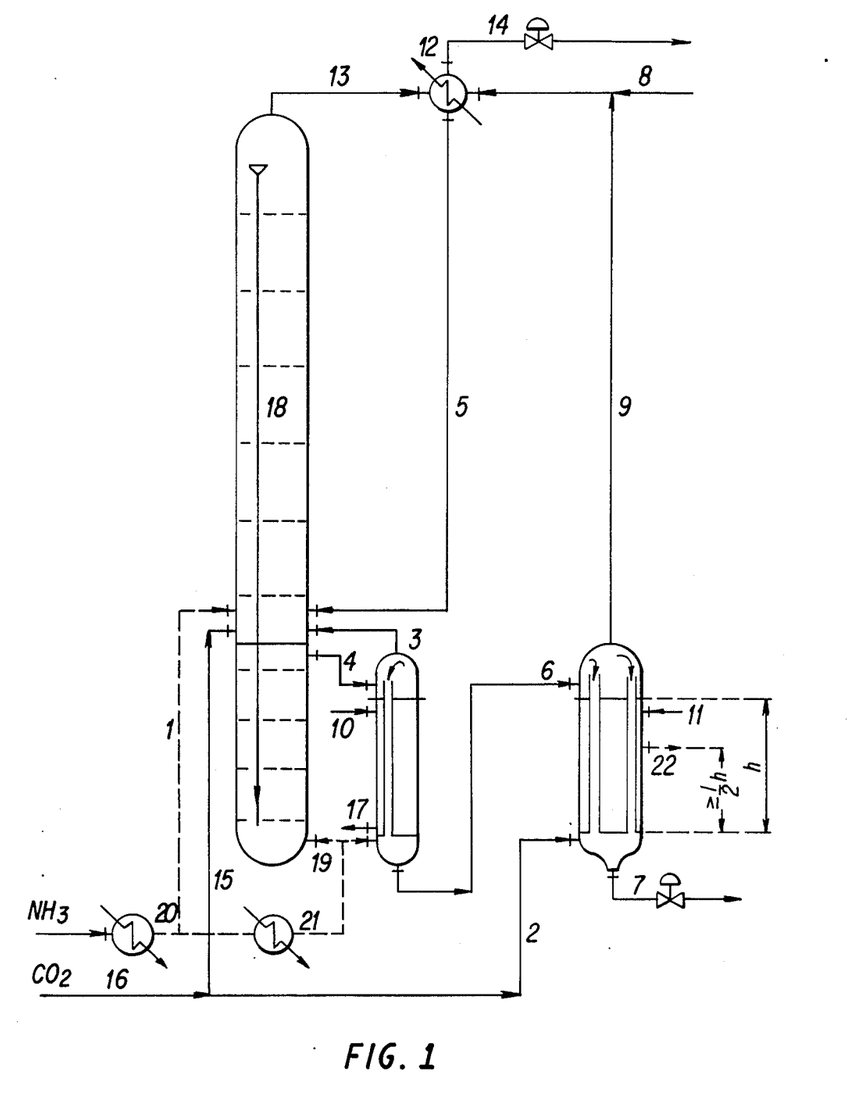

Following FIG. 1, urea is synthesized within a reactor subdivided into two sections, fitted with sieve trays. The liquid product flows over by gravity from the overlying into the underlying section through downcomer (18) and then it passes, through pipe (4), into a falling-film isobaric exchanger containing a tube bundle, where the non-reacted carbamate is almost totally decomposed by help of an $NH_3$ stream; the decomposition gases ($NH_3$ and $CO_2$) and part of the $NH_3$ excess flow back to the reactor (line 3). The solution (6) leaving the bottom of the $NH_3$ stripper contains 22% by weight of $CO_2$, with respect to urea (the 22% figure refers to $CO_2$, also if actually $CO_2$ is present as ammonium carbamate), and is then transferred to an isobaric $CO_2$ stripper, similar to the $NH_3$ stripper but having a greater number of exchanging pipes; in the $CO_2$ stripper the whole $CO_2$ amount required by the synthesis is injected to the bottom of the stripper and removes nearly all the last traces of $NH_3$. The solution (7) leaving the stripper's bottom is conveyed to the low pressure steps of the manufacturing process. The vapor ated in the condenser is at about 6 $Kg/cm^2$ (absolute) and its amount is such as to satisfy nearly all the steam requirements downstream of the I.D.R. high pressure loop. Data and results are reported on the following Table A.

TABLE A

| Line (from FIG. 1)* | 2 | | 6 | | 7 | | 9 | |
|---|---|---|---|---|---|---|---|---|
| T (°C.) | 130 | | 205 | | 172 | | 200 | |
| P ($Kg/cm^2$) | 200 | | 200 | | 200 | | 200 | |
| | Kg/h | % | Kg/h | % | Kg/h | % | Kg/h | % |
| $NH_3$ | — | — | 12466 | 36.1 | 3550 | 13.9 | 8916 | 47.0 |
| $CO_2$ | 9694 | 100 | 2698 | 7.8 | 2930 | 11.5 | 9462 | 50.8 |
| $H_2O$ | — | — | 6849 | 19.9 | 6600 | 25.8 | 249 | 1.3 |
| Urea | — | — | 12500 | 36.2 | 12500 | 48.8 | — | — |
| TOTAL | 9694 | 100 | 34513 | 100 | 25580 | 100 | 18627 | 100 |

*The balance is approximated because of the exclusion of inerts and biuret; percentages are by weight.

stream (9) leaves the head of the $CO_2$ stripper and is conveyed to a condenser, in admixture with the gases (13) coming from the reactor's head and with an aqueous solution (8) coming from the low-pressure process steps; a purge of residual gases (14) leaves the condenser, while a carbamate solution (5) is recycled to the reactor merely by means of gravity and without needing any recycle pump. The $NH_3$ requirement is preheated and fed to the reactor (line 1); it is thus possible to obtain a final urea solution (7) reach in urea and having a biuret percentage satisfactorily low, while wasting a very low amount of steam.

34513 Kg/h of an aqueous urea solution (6), the composition of which is reported on Table A, leave at 205° C. and 200 absolute $Kg/cm^2$, the bottom of the first isobaric stripper, ($NH_3$ stripper), heated by saturated steam (10) at 25 absolute $Kg/cm^2$; 9694 Kg/h of $CO_2$ (line 2) enter at 130° C. and 200 absolute $Kg/cm^2$, the bottom of the second isobaric stripper ($CO_2$ stripper), heated too by steam, at 25 absolute $Kg/cm^2$, only in the uppermost section of the tube-bundle; the condensate (condensed steam; hot liqiud water) leaves the stripper's mantel through nozzle (22).

22580 Kg/h of a final aqueous solution (7), the composition of which is on Table A, leave, at 172° C. and 200 absolute $Kg/cm^2$, the bottom of the same $CO_2$ stripper. Furtherly 18627 Kg/h of the fluid (9), the composition of which is in Table A, leaves, at 200° C., the head of the same $CO_2$ stripper; the ratio between the amount of carbamate (CBRU) leaving the $CO_2$ stripper and the amount of carbamate (CBRE) entering the same $CO_2$ stripper is:

CBRU:CBRE × 100 = 2930:2698 × 100 = 108.6%.

The rather small amount of steam (11), required by the heating of said $CO_2$ stripper, is such as to comply with the thermal balance. The low-pressure steam (12) gener-

EXAMPLE 2

(COMPARATIVE)

The test of example 1 was repeated, while totally suppressing the injection of steam to the $CO_2$ stripper and working therefore, in an adiabatic way; data and results are on Table B hereinafter. The CBRU:CBRE ratio is = 4646:2698 × 100 = 172.2%.

TABLE B

| Line (from FIG. 1) | 2 | | 6 | | 7 | | 9 | |
|---|---|---|---|---|---|---|---|---|
| T (°C.) | 130 | | 205 | | 165 | | 200 | |
| P ($Kg/cm^2$) | 200 | | 200 | | 200 | | 200 | |
| | Kg/h | % | Kg/h | % | Kg/h | % | Kg/h | % |
| $NH_3$ | — | — | 12466 | 36.1 | 4365 | 15.5 | 8101 | 50.5 |
| $CO_2$ | 9694 | 100 | 2698 | 7.8 | 4646 | 16.5 | 7746 | 48.3 |
| $H_2O$ | — | — | 6849 | 19.9 | 6650 | 23.6 | 199 | 1.2 |
| Urea | — | — | 12500 | 6.2 | 12500 | 44.4 | — | — |
| TOTAL | 9694 | 100 | 34513 | 100 | 28161 | 100 | 16046 | 100 |

The satisfactory removal of $NH_3$ is strictly bound, in this case, to an excessive formation of carbamate, which residual carbamate must be then decomposed within the low-pressure (finishing) loop, wasting a too great amount of thermal energy. The downstream low-pressure steps would require therefore apparatuses having much greater dimensions and it is well known how difficult it is the recovery, at a sufficiently satisfactory thermal level, of the heat supplied for the low-pressure decomposition of carbamate.

EXAMPLE 3

Operative conditions and composition of the process lines are recorded on Table 1.

Figure 2:
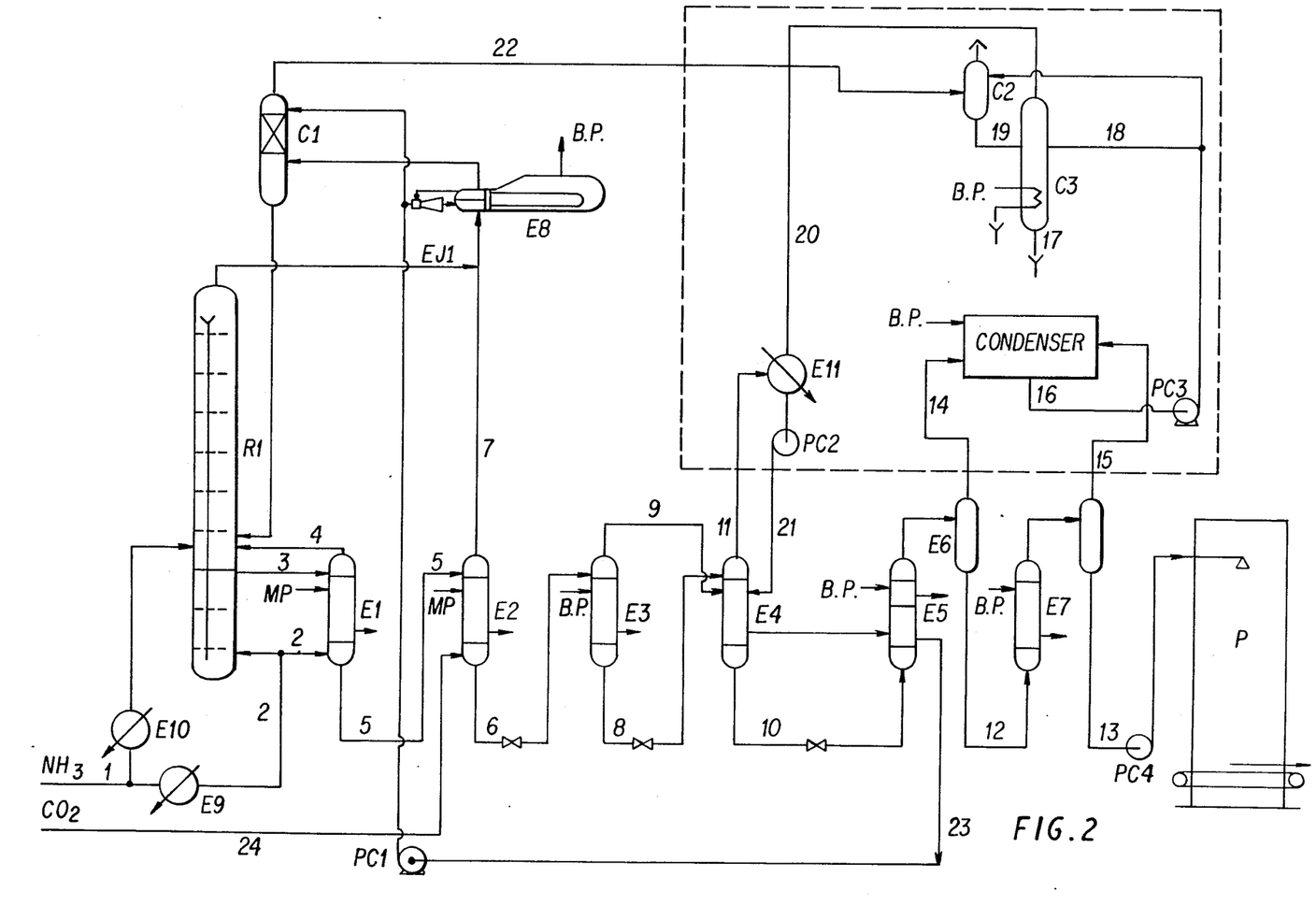

According to FIG. 2, the effluent (3), coming from reactor R1, was transferred to the first (falling-film) stripper (E1), isobaric with said reactor, in countercurrent to an $NH_3$ stream (2). We note incidentally that this stripper (E1) can obviously work also in a purely thermal way, namely without any injection of $NH_3$ from outside; furtherly the falling-film apparatus can be replaced by an "up-flow" apparatus, like the one indicated in FIG. 5. The solution leaving (E1) did flow into the second (falling-film) isobaric stripper (E2), in countercurrent to a $CO_2$ stream (24). The solution (6) leaving (E2) was flashed from 195 to 25 $Kg/cm^2$ (absolute) and did flow to the medium pressure (falling-film) still (E3) and the solution (8) leaving the bottom of (E3) was in turn flashed to 5 $Kg/cm^2$ (absolute) and transferred to the low-pressure (falling-film) still (E4). The steam condensates coming (at about 225° C.) from (E1) and (E2) were used for heating part of the $NH_3$ feed (at 200° C.), while the remnant portion of $NH_3$ was pre-heated (at 150°–160° C.) by means of recovery steam. The vapors (9) leaving the head of (E3) did supply, while condensing within the shell side, all the heat required by said still (E4) and by the first vacuum concentrator (E5), working at about 0.35 Kg/cm$^2$ (absolute), where the solution was concentrated up to about 85% b.w. (of urea); a further vacuum concentrator (E6), working too at 0.35 Kg/cm$^2$, and the final vacuum concentrator (E7), working at 0.05 Kg/cm$^2$ (absolute), brought the concentration up to 99.7% b.w., whereafter the molten urea (13) was ready to flow to a final prilling section (P) or to other treatment or use, of quite common nature.

The vapors (14) and (15) leaving the head of the vacuum concentrators (E6) and (E7) were condensed within a usual condensation system and were transferred, in the liquid state, to the recovery column (C3), wherefrom we got a recovery vapor (20), that was condensed in (E11), together with the head vapors (11) of the still (E4); the resulting condensate (21) entered the shell side of the same (E4) still. The condensed vapors (23) leaving (E5) were recompressed from 25 to 195 Kg/cm$^2$ (absolute) and then conveyed (in part, namely about 90%) to the high pressure (isobaric) condenser (E8), by means of ejector (EJ1); the remnant (about 10%) was used as a scrubbing liquid for the vent coming from the reactor (tower C1 in FIG. 2).

The steam balance is recorded on Table K; the urea output was 43,863 Kg/h and the medium-pressure steam consumption (at 25 Kg/cm$^2$) was:
13,158:43,863)×1000=300 Kg/t of urea and the low-pressure stream consumption (at 8 Kg/cm$^2$) was only: (40,120−36,845):43,863×1000=75 Kg/t.

In other words, the process was nearly self-supporting (as to the low-pressure steam requirement) and the medium-pressure steam consumption was limited to 300 Kg/t, what was indeed a new and surprising fact.

These results can be moreover improved by furtherly decreasing the low-pressure steam consumption; in particular, a new recovery system (i.e. recovery of $NH_3$ from the reaction waters), allowed to suppress completely the low-pressure steam. The gist of such a new system was the evaporation of said waters at the same pressure of the first vacuum concentrator (E5), the heat being supplied by a partial condensation of the vapors coming from (E4); said new system is described in detail hereinafter in Example 4.

EXAMPLE 4

Figure 3:
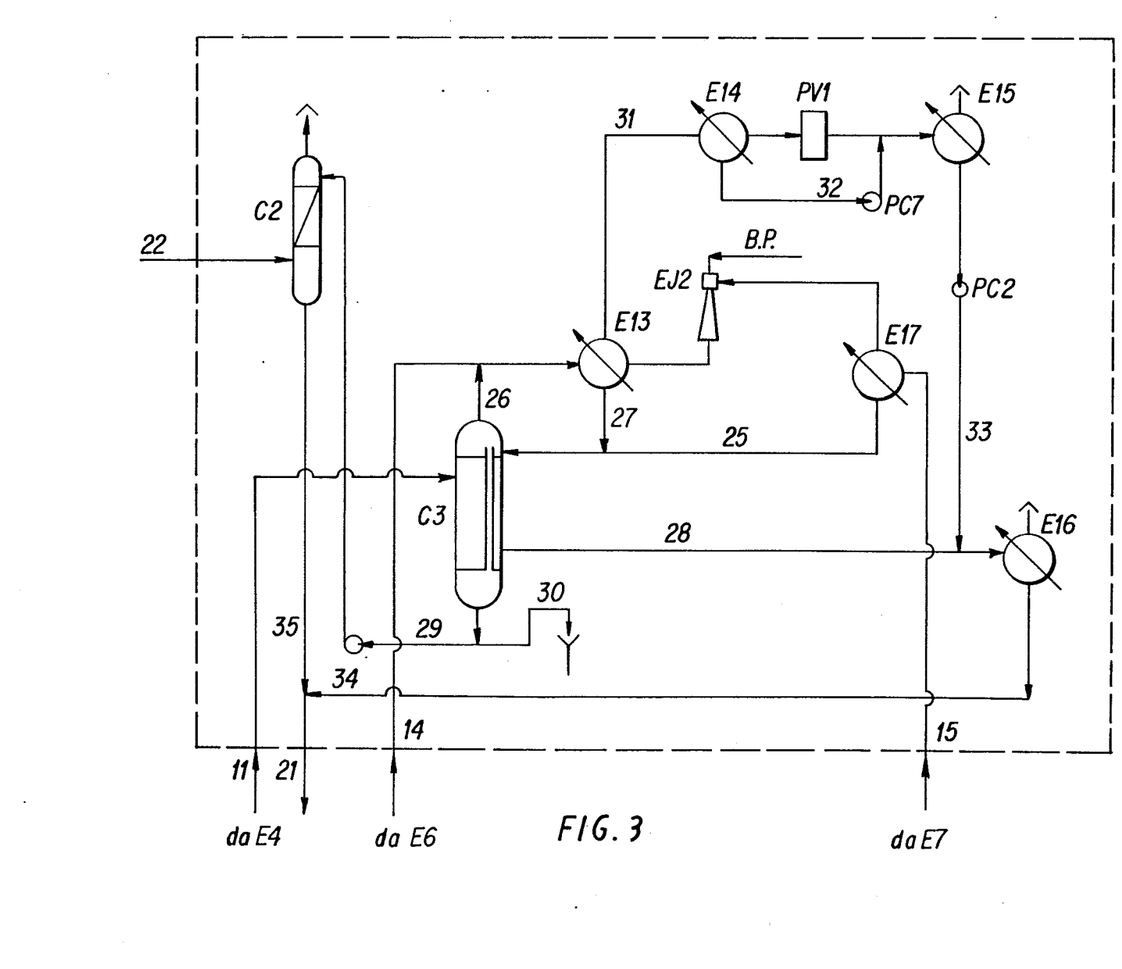

Example 3 was repeated, while replacing the recovery operations of FIG. 2 (dashed area) by the operations shown in FIG. 3; data and results were recorded on Table 2 and the steam balance on Table K.

According to said FIG. 3, to said Table 2 and to the preceeding FIG. 2, said vapors (14) coming from (E6) were condensed within said apparatus (E13), and said vapors (15) coming from (E7) were condensed (for the most part) first in the water-cooled apparatus (E17) and then in (E13), after a pressure increase, by means of ejector EJ2, driven by low-pressure steam. A condensed portion (25) of said vapors (15) did leave the (E17) cooler and entered the recovery tower (C3), consisting of a vertical falling-film tube-bundle, heated by the vapors (11) coming from the still (E4). Also the vapors (26) coming from the (C3) tower were entering said apparatus (E13), whereafter the liquid condensate (27) leaving same apparatus (E13) was recycled to said tower (C3), the bottom of which tower, practically free from $NH_3$ and about at 70° C., was partially wasted (line 30) and partially (line 29) utilized in (C2), namely in the scrubber of the vent gases (22). Said waste (30) to disposal was corresponding practically to the synthesis water plus the amount of steam used for the driving of ejector EJ2. The vapors (31), rich in recovered $NH_3$ and leaving the head of (E13), were partially condensed within the (E14) cooler; the condensate (through pump PC7) and the residual vapors (through vacuum pump PV1) were transferred to a condensation system (E15) working at about 1.5 Kg/cm$^2$ (absolute). The condensate herefrom was transferred, through pump (PC2), to the final condensation system (E16), working at 5 Kg/cm$^2$ (absolute), whereto flowed also the condensing mixture (28) coming from tower (C3), the cooling medium being the fresh $NH_3$ of the feed, which was thus pre-heated up to 70° C.

The thus obtained solution (34) joined solution (35) coming from scrubber (C2) and the mixture did flow to the shell side of the low-pressure still (E4). Such a recovery cycle allowed to remove all the synthesis water, while using recovery steam; the steam requirement (from outside) for the distillation (stills E3 and E4) and for the first vacuum concentrator (E5) was therefore null, while the power requirement for the vacuum pump (PV1) was merely about 2 Kwh/t of urea. With respect to example 1, we registered the output of an excess of low-pressure steam (at 8 Kg/cm$^2$, absolute), that can be calculated as follows (see Table K): (36,845−34,406):43,863×1000=55 Kg/t.

EXAMPLE 5

Figure 5:
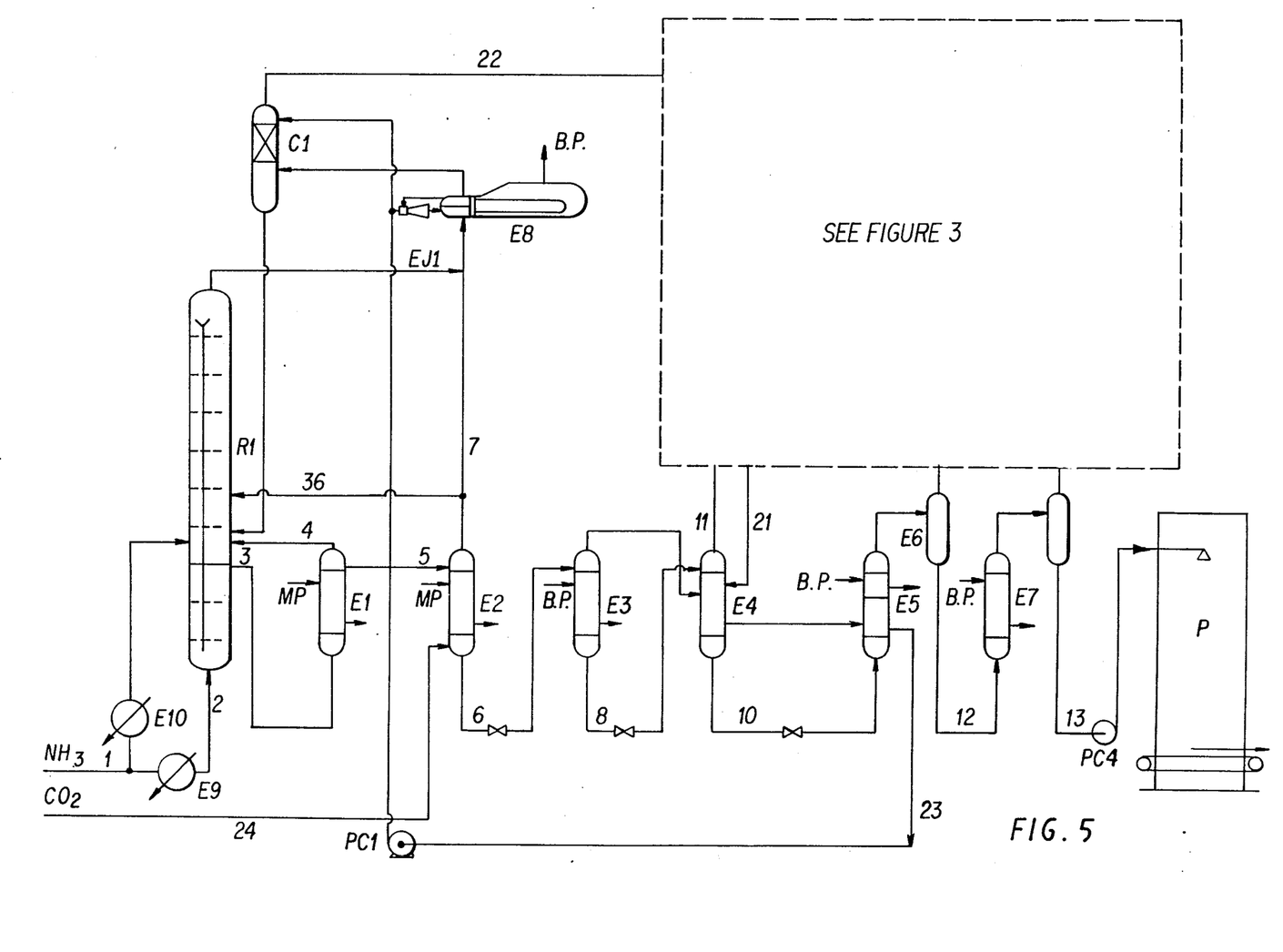

According to FIG. 3 and FIG. 5, example 4 was repeated, while modifying the first isobaric stripper (E1), which was an "up-flow" equicurrent apparatus, instead of the former falling-film (countercurrent) exchanger; no stripping gas was injected from outside, as a coadjuvant agent.

The working of second isobaric stripper (E2) was adiabatic; no indirect heat (namely no condensing steam) was supplied to (E2) and the displacement of the $NH_3$ excess was merely bound to the parallel formation of carbamate, while a "self-cooling" of the solution was registered. Moreover, a portion (36) of the vapors leaving the head of said second stripper (E2) was recycled directly to the synthesis reactor (R1), because of the thermal balance, in a point higher than the inlet of the vapors coming from said first stripper (E1). Within said reactor the $NH_3:CO_2$ molar ratio was 4.5, the $H_2O/CO_2$ molar ratio was 0.4 and the carbamate conversion per pass was 73%. Data and results are on Table 3; the $NH_3$ recovery cycle (from the synthesis waters) is still the cycle of example 4 and the steam balance is recorded on Table K. The reduction of the medium-pressure steam consumption to 150 Kg/t (see Table K) allows to approximate considerably the exciting threshold of a steam requirement completely null, namely the thermal independence.

EXAMPLE 6

Figure 6:
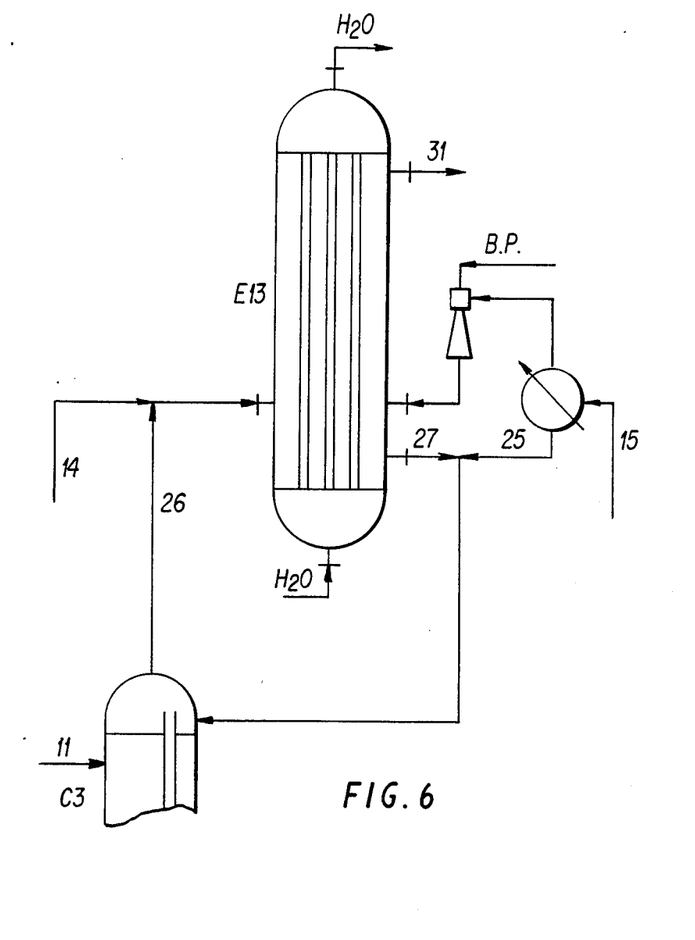

Example 5 was repeated, but for the differences hereinafter. More heat was supplied to the (E3) still (by means of an increase of the recovery steam coming from (E8), namely more than the heat required by (E4) and (E5); the consequent excess of heat was recovered by cooling the vapors (9) leaving (E3), rich in NH₃ and CO₂, within a proper exchanger (E10/bis), which preheated the NH₃ fresh feed (see FIG. 6). Such a new exchanger was connected in series with (E4) and (E5) and was fed not only by vapors (9) hereinabove but also by a liquid phase (21) in order to speed up the condensation of the same vapors (9) (see FIG. 6). The steam balance was recorded on Table K. Should the exchanger E10/bis be connected in parallel, results would be nearly the same.

TABLE K

| AMOUNTS OF STEAM | EXAMPLE 1 | EXAMPLE 2 | EXAMPLE 3 | EXAMPLE 4 |
|---|---|---|---|---|
| Waste of medium pressure saturated steam (at 25 Kg/cm², absolute): | | | | |
| to the first isobaric stripper (E1) | 10088 Kg/h | 10088 Kg/h | 6580 Kg/h | 6580 Kg/h |
| to the second isobaric stripper (E2) | 3070 Kg/h | 3070 Kg/h | — | — |
| Total | 13158 Kg/h | 13158 Kg/h | 6580 Kg/h | 6580 Kg/h |
| Waste of low-pressure saturated steam (at 8 Kg/cm², absolute): | | | | |
| to still (E3) | 17545 Kg/h | 17545 Kg/h | 15483 Kg/h | 17676 Kg/h |
| to vacuum concentrator (E6) | 5263 Kg/h | 5263 Kg/h | 5263 Kg/h | 5263 Kg/h |
| to vacuum concentrator (E7) | 3948 Kg/h | 3948 Kg/h | 3948 Kg/h | 3948 Kg/h |
| to vacuum system (driving of a battery of ejectors) | 1754 Kg/h | 420 Kg/h | 420 Kg/h | 420 Kg/h |
| to recovery tower (C3) | 4380 Kg/h | — | — | — |
| to NH₃ pre-heating | 4380 Kg/h | 4380 Kg/h | 5910 Kg/h | 1530 Kg/h |
| to steam-tracings | 2850 Kg/h | 2850 Kg/h | 2850 Kg/h | 2850 Kg/h |
| Total | 40120 Kg/h | 34406 Kg/h | 33874 Kg/h | 31687 Kg/h |
| Recovery of saturated steam (at 8 Kg/cm², absolute) From (E8) | 36845 Kg/h | 36845 Kg/h | 31669 Kg/h | 31669 Kg/h |
| Summary (unitary amounts) | | | | |
| Waste of 25 Kg/cm² steam (Kg/t of urea) | 300 Kg/t | 300 Kg/t | 150 Kg/t | 150 Kg/t |
| Recovery (balance) of 8 Kg/cm² steam | −75 Kg/t* | +55 Kg/t | −50 Kg/t* | — |

*Waste

TABLE 1

| LINE | 1 | | 2 | | 3 | | 4 | | 5 | | 6 | |
|---|---|---|---|---|---|---|---|---|---|---|---|---|
| State | Liquid | | Gas | | Liquid | | Vapor | | Liquid | | Liquid | |
| P (kg/cm² abs.) | 195 | | 195 | | 195 | | 195 | | 195 | | 195 | |
| T (°C.) | 200 | | 200 | | 194 | | 195 | | 203 | | 175 | |
| COMPOSITION | kg/h | % b.w. | kg/h | % b.w. | kg/h | % b.w. | kg/h | % b.w. | kg/h | % b.w. | kg/h | % b.w. |
| Urea | — | — | — | — | 43,863 | 34.50 | — | — | 43,863 | 37.22 | 43,863 | 45.77 |
| NH₃ | 24,856 | 100.00 | 7,500 | 100.00 | 45,634 | 35.89 | 11,396 | 67.81 | 41,738 | 35.42 | 14,135 | 14.76 |
| CO₂ | — | — | — | — | 13,789 | 10.84 | 5,043 | 30.00 | 8,746 | 7.42 | 15,343 | 16.01 |
| H₂O | — | — | — | — | 23,865 | 18.77 | 367 | 2.19 | 23,498 | 19.94 | 22,480 | 23.46 |
| TOTAL | 24,856 | 100.00 | 7,500 | 100.00 | 127,151 | 100.00 | 16,806 | 100.00 | 117,845 | 100.00 | 95,821 | 100.00 |

| LINE | 7 | | 8 | | 9 | | 10 | | 11 | | 12 | |
|---|---|---|---|---|---|---|---|---|---|---|---|---|
| State | Vapor | | Liquid | | Vapor | | Liquid | | Vapor | | Liquid | |
| P (kg/cm² abs.) | 195 | | 25 | | 25 | | 5 | | 5 | | 0,35 | |
| T (°C.) | 200 | | 157 | | 160 | | 135 | | 135 | | 115 | |
| COMPOSITION | kg/h | % b.w. | kg/h | % b.w. | kg/h | % b.w. | kg/h | % b.w. | kg/h | % b.w. | kg/h | % b.w. |
| Urea | — | — | 43,863 | 60.20 | — | — | 43,863 | 72.00 | — | — | 43,863 | 92.26 |
| NH₃ | 27,603 | 50.94 | 5,422 | 7.44 | 8,713 | 37.95 | 914 | 1.50 | 4,508 | 37.74 | 119 | 0.25 |
| CO₂ | 25,569 | 47.18 | 2,889 | 3.96 | 12,454 | 54.25 | 805 | 0.50 | 2,584 | 21.64 | 47 | 0.10 |
| H₂O | 1,018 | 1.88 | 20,690 | 28.40 | 1,790 | 7.80 | 15,839 | 26.00 | 4,851 | 40.62 | 3,516 | 7.39 |
| TOTAL | 54,190 | 100.00 | 72,864 | 100.00 | 22,957 | 100.00 | 60,921 | 100.00 | 11,943 | 100.00 | 47,545 | 100.00 |

| LINE | 13 | | 14 | | 15 | | 16 | | 17 | | 18 | |
|---|---|---|---|---|---|---|---|---|---|---|---|---|
| State | Liquid | | Vapor | | Vapor | | Liquid | | Liquid | | Liquid | |
| P (kg/cm² abs.) | 0,05 | | 0,35 | | 0,05 | | — | | — | | — | |
| T (°C.) | 140 | | 120 | | 140 | | 40 | | 40 | | 40 | |
| COMPOSITION | kg/h | % b.w. | kg/h | % b.w. | kg/h | % b.w. | kg/h | % b.w. | kg/h | % b.w. | kg/h | % b.w. |
| Urea | 43,863 | 99.70 | — | — | — | — | — | — | — | — | — | — |
| NH₃ | — | — | 795 | 5.94 | 119 | 3.35 | 914 | 4.89 | — | — | 758 | 4.89 |
| CO₂ | — | — | 258 | 1.93 | 47 | 1.32 | 305 | 1.63 | — | — | 253 | 1.63 |
| H₂O | 132 | 0.30 | 12,323 | 92.13 | 3,384 | 95.33 | 17,457 | 93.48 | 14,777 | 100.00 | 14,489 | 93.48 |
| TOTAL | 43,995 | 100.00 | 13,376 | 100.00 | 3,550 | 100.00 | 18,676 | 100.00 | 14,777 | 100.00 | 15,500 | 100.00 |

| LINE | 19 | | 20 | | 21 | | 22 | | 23 | | 24 | |
|---|---|---|---|---|---|---|---|---|---|---|---|---|
| State | Liquid | | Vapor | | Liquid | | Gas* | | Liquid | | Gas | |
| P (kg/cm² abs.) | 5 | | 5 | | 25 | | 195 | | 25 | | 195 | |
| T (°C.) | 60 | | 80 | | 50 | | about 195 | | 125 | | 130 | |
| COMPOSITION | kg/h | % b.w. | kg/h | % b.w. | kg/h | % b.w. | kg/h | % b.w. | kg/h | % b.w. | kg/h | % b.w. |
| Urea | — | — | — | — | — | — | — | — | — | — | — | — |
| NH₃ | 304 | 8.73 | 1,062 | 25.25 | 5,570 | 34.49 | 148 | — | 14,283 | 36.52 | — | — |
| CO₂ | 210 | 6.03 | 463 | 11.01 | 3,047 | 18.87 | 158 | — | 15,501 | 39.64 | 32,166 | 100.00 |
| H₂O | 2,968 | 85.24 | 2,680 | 63.74 | 7,531 | 46.64 | — | — | 9,321 | 23.84 | — | — |
| TOTAL | 3,482 | 100.00 | 4,205 | 100.00 | 16,148 | 100.00 | 306 | | 39,105 | 100.00 | 32,166 | 100.00 |

*Inert gas + NH₃ + CO₂

TABLE 2

| LINE | 25 | | 26 | | 27 | | 28 | | 29 | | 30 | | 31 | |
|---|---|---|---|---|---|---|---|---|---|---|---|---|---|---|
| State | Liquid | | Vapor | | Liquid | | Liquid + vapor | | Liquid | | Liquid | | Vapor | |
| P (kg/cm² abs.) | 0,05 | | 0,35 | | 0,35 | | 5 | | 0,35 | | 1 | | 0,35 | |
| T (°C.) | 40 | | 60 | | 40 | | 85 | | 70 | | 70 | | 50 | |
| COMPOSITION | kg/h | % b.w. | kg/h | % b.w. | kg/h | % b.w. | kg/h | % b.w. | kg/h | % b.w. | kg/h | % b.w. | kg/h | % b.w. |
| Urea | — | — | — | — | — | — | — | — | — | — | — | — | — | — |
| $NH_3$ | 71 | 2.08 | 176 | 4.83 | 105 | 0.75 | 4,508 | 37.74 | — | — | — | — | 914 | 25.40 |
| $CO_2$ | 47 | 1.38 | 75 | 2.05 | 28 | 0.20 | 2,584 | 21.64 | — | — | — | — | 305 | 8.47 |
| $H_2O$ | 3,295 | 96.54 | 3,400 | 93.12 | 13,852 | 99.05 | 4,851 | 40.62 | 300 | 100.00 | 13,447 | 100.00 | 2,380 | 66.13 |
| TOTAL | 3,413 | 100.00 | 3,651 | 100.00 | 13,985 | 100.00 | 11,943 | 100.00 | 300 | 100.00 | 13,447 | 100.00 | 3,599 | 100.00 |

| LINE | 32 | | 33 | | 34 | | 35 | |
|---|---|---|---|---|---|---|---|---|
| State | Liquid | | Liquid | | Liquid | | Liquid | |
| P (kg/cm² abs.) | 0,35 | | 5 | | 5 | | 25 | |
| T (°C.) | 50 | | 40 | | 50 | | 50 | |
| COMPOSITION | kg/h | % b.w. | kg/h | % b.w. | kg/h | % b.w. | kg/h | % b.w. |
| Urea | — | — | — | — | — | — | — | — |
| $NH_3$ | 390 | 12.93 | 914 | 25.40 | 5,422 | 34.88 | 148 | 24.42 |
| $CO_2$ | 305 | 10.12 | 305 | 8.47 | 2,889 | 18.59 | 158 | 26.07 |
| $H_2O$ | 2,320 | 76.95 | 2,580 | 66.13 | 7,231 | 46.53 | 300 | 49.51 |
| TOTAL | 3,015 | 100.00 | 3,599 | 100.00 | 15,542 | 100.00 | 606 | 100.00 |

TABLE 3

| LINE | 1 | | 2 | | 3 | | 4 | | 5 | | 6 | |
|---|---|---|---|---|---|---|---|---|---|---|---|---|
| State | Liquid | | Gas | | Gas | | Vapor | | Liquid | | Liquid | |
| P (kg/cm² abs.) | 190 | | 190 | | 190 | | 190 | | 190 | | 190 | |
| T (°C.) | 200 | | 190 | | 200 | | 200 | | 200 | | 165 | |
| COMPOSITION | kg/h | % b.w. | kg/h | % b.w. | kg/h | % b.w. | kg/h | % b.w. | kg/h | % b.w. | kg/h | % b.w. |
| Urea | — | — | — | — | 43,863 | 34.30 | — | — | 43,863 | 37.27 | 43,863 | 49.25 |
| $NH_3$ | 24,856 | 100.00 | 3,500 | 100.00 | 51,752 | 40.47 | 9,697 | 95.16 | 42,055 | 35.73 | 12,055 | 13.54 |
| $CO_2$ | | | | | 11,897 | 9.30 | 343 | 3.37 | 11,554 | 9.82 | 13,915 | 15.63 |
| $H_2O$ | | | | | 20,367 | 15.93 | 150 | 1.47 | 20,217 | 17.18 | 19,217 | 21.58 |
| TOTAL | 24,856 | 100.00 | 3,500 | 100.00 | 127,879 | 100.00 | 10,190 | 100.00 | 117,689 | 100.00 | 89,050 | 100.00 |

| LINE | 7 | | 8 | | 9 | | 10 | | 11 | | 12 | |
|---|---|---|---|---|---|---|---|---|---|---|---|---|
| State | Vapor | | Liquid | | Vapor | | Liquid | | Vapor | | Liquid | |
| P (kg/cm² abs.) | 190 | | 25 | | 25 | | 5 | | 5 | | 0,35 | |
| T (°C.) | 195 | | 155 | | 155 | | 135 | | 135 | | 115 | |
| COMPOSITION | kg/h | % b.w. | kg/h | % b.w. | kg/h | % b.w. | kg/h | % b.w. | kg/h | % b.w. | kg/h | % b.w. |
| Urea | — | — | 43,863 | 61.31 | — | — | 43,863 | 72.00 | — | — | 43,863 | 92.26 |
| $NH_3$ | 28,088 | 49.34 | 4,792 | 6.70 | 7,263 | 41.48 | 914 | 1.50 | 3,878 | 36.51 | 119 | 0.25 |
| $CO_2$ | 27,906 | 49.02 | 4,515 | 6.31 | 9,400 | 53.69 | 305 | 0.50 | 4,210 | 39.64 | 47 | 0.10 |
| $H_2O$ | 936 | 1.64 | 18,372 | 25.68 | 845 | 4.83 | 15,839 | 26.00 | 2,533 | 23.85 | 3,516 | 7.39 |
| TOTAL | 56,930 | 100.00 | 71,542 | 100.00 | 17,508 | 100.00 | 60,921 | 100.00 | 10,621 | 100.00 | 47,545 | 100.00 |

| LINE | 13 | | 14 | | 15 | | 21 | | 22 | | 23 | |
|---|---|---|---|---|---|---|---|---|---|---|---|---|
| State | Liquid | | Vapor | | Vapor | | Liquid | | Gas* | | Liquid | |
| P (kg/cm² abs.) | 0,05 | | 0,35 | | 0,05 | | 25 | | 190 | | 25 | |
| T (°C.) | 140 | | 120 | | 140 | | 70 | | about 190 | | 125 | |
| COMPOSITION | kg/h | % b.w. | kg/h | % b.w. | kg/h | % b.w. | kg/h | % b.w. | kg/h | % b.w. | kg/h | % b.w. |
| Urea | 43,863 | 99.70 | — | — | — | — | — | — | — | — | — | — |
| $NH_3$ | — | — | 795 | 5.94 | 119 | 3.35 | 4,940 | 33.32 | 148 | — | 12,203 | 37.74 |
| $CO_2$ | — | — | 258 | 1.93 | 47 | 1.32 | 4,673 | 31.52 | 158 | — | 14,073 | 43.52 |
| $H_2O$ | 132 | 0.30 | 12,323 | 92.13 | 3,384 | 95.33 | 5,213 | 35.16 | — | — | 6,058 | 18.74 |
| TOTAL | 43,995 | 100.00 | 13,376 | 100.00 | 3,550 | 100.00 | 14,826 | 100.00 | 306 | — | 32,334 | 100.00 |

| LINE | 24 | | 25 | | 26 | | 27 | | 28 | | 29 | |
|---|---|---|---|---|---|---|---|---|---|---|---|---|
| State | Gas | | Liquid | | Vapor | | Liquid | | Liquid + vapor | | Liquid | |
| P (kg/cm² abs.) | 190 | | 0,05 | | 0,35 | | 0,35 | | 5 | | 0,35 | |
| T (°C.) | 130 | | 40 | | 60 | | 40 | | 85 | | 70 | |
| COMPOSITION | kg/h | % b.w. | kg/h | % b.w. | kg/h | % b.w. | kg/h | % b.w. | kg/h | % b.w. | kg/h | % b.w. |
| Urea | — | — | — | — | — | — | — | — | — | — | — | — |
| $NH_3$ | — | — | 71 | 2.08 | 176 | 4.83 | 105 | 0.75 | 3,878 | 36.51 | — | — |
| $CO_2$ | 32,166 | 100.00 | 47 | 1.38 | 75 | 2.05 | 28 | 0.20 | 4,210 | 39.64 | — | — |
| $H_2O$ | — | — | 3,295 | 96.54 | 3,400 | 93.12 | 13,852 | 99.05 | 2,533 | 23.85 | 300 | 100.00 |
| TOTAL | 32,166 | 100.00 | 3,413 | 100.00 | 3,051 | 100.00 | 13,985 | 100.00 | 10,621 | 100.00 | 300 | 100.00 |

| LINE | 30 | | 31 | | 32 | | 33 | | 34 | | 35 | | 36 | |
|---|---|---|---|---|---|---|---|---|---|---|---|---|---|---|
| State | Liquid | | Vapor | | Liquid | | Liquid | | Liquid | | Liquid | | Vapor | |
| P (kg/cm² abs.) | 1 | | 0,35 | | 0,35 | | 5 | | 5 | | 25 | | 190 | |
| T (°C.) | 70 | | 50 | | 40 | | 40 | | 50 | | 50 | | 200 | |
| COMPOSITION | kg/h | % b.w. | kg/h | % b.w. | kg/h | % b.w. | kg/h | % b.w. | kg/h | % b.w. | kg/h | % b.w. | kg/h | % b.w. |
| Urea | — | — | — | — | — | — | — | — | — | — | — | — | — | — |
| $NH_3$ | — | — | 914 | 25.40 | 390 | 12.93 | 914 | 25.40 | 4,792 | 33.70 | 148 | 24.42 | 1,912 | 49.34 |
| $CO_2$ | — | — | 305 | 8.47 | 305 | 10.12 | 305 | 8.47 | 4,515 | 31.75 | 158 | 26.07 | 1,899 | 49.01 |
| $H_2O$ | 13,447 | 100.00 | 2,380 | 66.13 | 2,320 | 76.95 | 2,390 | 66.13 | 4,913 | 34.55 | 300 | 49.51 | 64 | 1.65 |

TABLE 3-continued

| TOTAL | 13,447 | 100.00 | 3,599 | 100.00 | 3,015 | 100.00 | 3,599 | 100.00 | 14,220 | 100.00 | 606 | 100.00 | 3,875 | 100.00 |
|---|---|---|---|---|---|---|---|---|---|---|---|---|---|---|

*Inert gas + NH₃ + CO₂

What we claim is:

1. A process for the displacement to the gaseous phase, at 80–250 Kg/cm², of the excess of $NH_3$ contained in an aqueous urea solution, coming, at 150°–230° C., from a former stripping, isobaric with the urea synthesis, and containing also $CO_2$ as ammonium carbamate, the $CO_2$ being at most 25% b.w. of the urea, wherein the displacement is performed by means of a $CO_2$ stripping within a falling-film exchanger, hereinafter $CO_2$ stripper, isobaric too with said synthesis, the amount of carbamate leaving the bottom of the $CO_2$ stripper being substantially equal to (or comprised between 100 and 150% of) the amount of carbamate entering the same stripper, characterized in that the global $NH_3:CO_2$ ratio, in the solution entering the $CO_2$ stripper, is from 2 to 8 b.w. and in that heat is supplied only to the uppermost portion of the pipes of the $CO_2$ stripper, wherein the surface ratio between the lowermost portion and said uppermost portion is at least 1:1 and wherein the residence time ratio between said lowermost portion and said uppermost portion is at least 1/1, the residence time in said uppermost portion being from 1 to 3 s.

2. A process according to claim 1, wherein the surface of said uppermost portion is from 1/5 to ½, preferably from 1/5 to ⅓, of the total surface.

3. A process according to claim 1, wherein the pressure, during the $CO_2$ stripping, is from 130 to 220, preferably from 170 to 210 Kg/cm², wherein the inlet temperature of the urea solution fed to the $CO_2$ stripper is from 190 to 220 preferably 200° to 210° C. and wherein the outlet temperature of the final solution, leaving the $CO_2$ stripper, is from 150 to 210, preferably 160 to 190 and even better 160° to 175° C., provided the same outlet temperature be lower than the inlet temperature on the top of the $CO_2$ stripper and provided the temperature of the $CO_2$ injected as a stripping agent, is from 80° to 140° C.

4. A process according to claim 1, wherein the ratio A between the exchanging surface of the $CO_2$ stripper ($S_{CO2}$) and the exchanging surface ($S_{NH3}$) of the preceeding stripper is given by the expression:

$$A = S_{CO2} : S_{NH3} > 1.$$

5. A process according to claim 1, characterized in that the global $NH_3CO_2$ ratio, in the solution entering the $CO_2$ stripper, is from 3 to 6 b.w. and in that the surface ratio between said lowermost portion and said uppermost portion is at least 2/1, wherein the residence time ratio between said lowermost portion and said uppermost portion is at least 2:1, the residence time in said uppermost portion being from 1.5 to 2.5 s, provided the outlet temperature of the final solution, leaving the $CO_2$ stripper, be from 160° to 190° C. and provided the same outlet temperature be lower than the inlet temperature on the top of the $CO_2$ stripper.

6. A process according to claim 5, wherein said global $NH_3:CO_2$ ratio is from 4 to 5.5 b.w., said surface ratio is from 2 to 4 and said residence time ratio is from 2 to 4, provided said outlet temperature be from 160° to 175° C.

7. An I.D.R. process for the manufacture of urea, comprising two subsequent loops, wherein:

(A) in the first (high pressure) loop the solution coming from the synthesis zone contains, after the first isobaric stripper (E1), a strong $NH_3$ excess ($NH_3:CO_2 \geq 6$ by moles) and a low $CO_2$ percentage ($CO_2$: urea ≦ 25% b.w.) and contains, before the second isobaric stripper (E2), an amount of ammonium carbamate comprised from 100 to 150% (preferably from 100 to 130%) of the amount of carbamate contained in the solution leaving the same (E2) stripper, wherein the consequent overproduction of carbamate (in E2) releases such an amount of heat to displace a major proportion of the residual $NH_3$ excess contained therein;

(B) in the second (low pressure) loop, the solution leaving (E2) is flashed at 20–30 ata and enters a first (medium pressure) still (E3), heated indirectly and completely by a low pressure recovery steam, coming from the isobaric condensation (in E8) of the vapors leaving the top of (E2), said recovery steam having such a thermal level to decompose at least said overproduction of carbamate, originated in (E2);

(C) the solution leaving (E3) is flashed substantially at 5 ata and enters a second (low pressure) still (E4) and then a vacuum concentrator (E5), wherein the heat of the vapors leaving the head of (E3), rich in $NH_3$ and $CO_2$, is exploited for the working run of (E4) and (E5).

8. A process according to claim 7, wherein:

the pressure of the "high pressure" loop is from 120 to 250 Kg/cm²;

the temperature of the solution leaving the first isobaric stripper (E1) is from 150° to 230° C.;

said $NH_3:CO_2$ molar ratio ($\geq 6$ by moles at the outlet of the first stripper) concerns the total amounts of $NH_3$ and $CO_2$, also if chemically bound, but for the amounts bound in the form of urea;

said recovery steam (coming from E8) is at a pressure $\geq 6.5$ absolute atmospheres;

the working pressure of the process side of said vacuum concentrator (E5) is substantially 0.35 absolute atm.;

the ratio between the fresh $CO_2$, fed to the second isobaric stripper ($CO_2$ inj.), and the carbamate (CBE) entering the same stripper attains a very high level, namely:

($CO_2$ inj.):(CBE) > 2 (by moles).

9. A process according to claim 7, wherein said first isobaric stripper (E1) of the I.D.R. process is a vertical heat exchanger having a tube bundle and being selected from the group comprising the "falling-film" and the "upflow" exchangers.

10. A process according to claim 7, wherein the solution leaving (E5) is furtherly concentrated in (E6) exploiting the heat of the recovery steam hereinabove, and the resulting concentrated solution is transferred to a final vacuum concentrator (E7), wherein the vapors leaving the vacuum concentrators (E5, E6 and E7), containing some amounts of $NH_3$ and $CO_2$, are condensed in an usual way and wherein a recovery tower (C3) allows to obtain a recovery stream to be condensed (in E11), together with the vapors coming from said still (E4), the resulting condensate being recycled to said (E4) still (shell side) and the condensed vapors leaving (E5) being recompressed and recycled to the high pressure loop.

11. A Process according to claim 10, wherein (within said second stripper E2) the ratio:

$$R = \frac{\text{uppermost surface of the pipes, heated by condensing steam}}{\text{remnant portion of the surface of the pipes}}$$

is $R \leqq 1$, and preferably from $\frac{1}{2}$ to $\frac{1}{4}$.

12. A process according to claim 10, wherein the residence time of the urea solution, in said uppermost portion of the exchanger E2 is from 1.5 to 3 s (preferably from 1.5 to 2.5 s).

13. A process according to claim 10, wherein:
    (a) the urea synthesis is performed at 150°–250° C. and 170–220 atmospheres;
    (b) the temperature of the solution entering said second stripper (E2) is from 190° to 220° C.;
    (c) the temperature of the solution leaving the bottom of the same stripper (E2) is from 150° to 190° C., preferably from 160° to 190° C. and even better from 160° to 175° C.;
    (d) the temperature of the $CO_2$, injected as a stripping agent into the same stripper (E2), is from 80° to 140° C.;
    (e) the solution leaving said first stripper (E1) and entering said second stripper (E2) contains such a low amount of $CO_2$ that:

$CO_2$: urea $\leqq 22\%$ b.w.;

(f) the $NH_3$:$CO_2$ molar ratio, in said solution entering said second stripper (E2), is equal to or higher than 10:1.

14. A process according to claim 10, wherein a portion of the vapors leaving the head of said stripper (E2) is recycled directly to the synthesis reactor, without flowing through high pressure condenser (E8), in a point higher than the inlet of the vapors coming from said first stripper (E1).

15. A process according to claim 10, wherein the vapors (14) coming from vacuum concentrators (E5) and (E6) are condensed within a water-cooled apparatus (E13), whereinto is conveyed also a portion of the vapors (15) coming from the final vacuum concentrator (E7) (previously compressed in E12), the remnant portion (25) being fed, as a liquid phase, to the recovery tower (C3), wherein said (C3) tower contains a vertical falling-film tube bundle, heated by the vapors (11) coming from said low-pressure still (E4), and wherein the vapors (26), containing $NH_3$ and coming from said (C3) tower, are condensed too within said water-cooled apparatus (E13), whereafter the liquid condensate (27) leaving said apparatus (E13) is recycled to said tower (C3), the bottom of which tower, practically free from $NH_3$, is partially wasted (line 30) and partially utilized (line 29) for the scrubbing of the synthesis vent (22).

* * * * *